United States Patent [19]

Nishihira et al.

[11] Patent Number: 5,292,917

[45] Date of Patent: Mar. 8, 1994

[54] PROCESS FOR PURIFYING DIMETHYL CARBONATE

[75] Inventors: Keigo Nishihira; Shinichi Yoshida; Shuji Tanaka, all of Ube, Japan

[73] Assignee: Ube Industries, Ltd., Yamaguchi, Japan

[21] Appl. No.: 56,891

[22] Filed: May 5, 1993

Related U.S. Application Data

[63] Continuation of Ser. No. 837,881, Feb. 9, 1992.

[30] Foreign Application Priority Data

Feb. 26, 1991 [JP] Japan .................................. 2-053148

[51] Int. Cl.$^5$ ............................................. C07C 69/96
[52] U.S. Cl. .................................................. 558/277
[58] Field of Search ........................................... 558/277

[56] References Cited

U.S. PATENT DOCUMENTS 4,467,109  8/1984  Tahara et al. ...................... 560/193
4,663,477  5/1987  Crandall et al. .................... 560/204

Primary Examiner—Mary C. Lee
Assistant Examiner—Michael Ambrose
Attorney, Agent, or Firm—Finnegan, Henderson, Farabow, Garrett & Dunner

[57] ABSTRACT

Disclosed a process for purifying dimethyl carbonate which comprises distillating a mixture of dimethyl carbonate and methanol in the presence of dimethyl oxalate to separate and remove methanol.

4 Claims, 1 Drawing Sheet

○ Without addition of dimethyl oxalate
● Addition of dimethyl oxalate

PROCESS FOR PURIFYING DIMETHYL CARBONATE

This is a continuation of application Ser. No. 07/837,881, filed Feb. 20, 1992, pending.

BACKGROUND OF THE INVENTION

This invention relates to a process for purifying dimethyl carbonate which is useful as a synthesis starting material for an aromatic polycarbonate and various chemical products and as a solvent. More particularly, it relates to a process for purifying dimethyl carbonate which comprises distillating and separating methanol to purify dimethyl carbonate by co-presenting dimethyl oxalate in order to prevent reacting carbon monoxide and an ester of nitrous acid in the presence of a specific catalyst with high yield.

As a process for preparing dimethyl carbonate, there have been practiced by, for example, the method of reacting carbon monoxide, methanol and an acid by using copper chloride (Japanese Patent Publications No. 11129/1970 and No. 45655/1980), the method of interesterifying a cyclic carbonate such as ethylene carbonate with methanol in the presence of a catalyst (U.S. Pat. Nos. 3,642,858 and 3,803,201, and Japanese Patent Publication No. 27658/1985), and the method of subjecting to vapor reaction of carbon monoxide and nitrite in the presence of a catalyst (Japanese Unexamined Patent Publications No. 274816/1989 and No. 201146/1990). However, in either of the methods, dimethyl carbonate can be obtained as a mixture with methanol so that separation from methanol is indispensable for purifying dimethyl methyl carbonate. Dimethyl carbonate and methanol constitute azeotropic mixture in a composition ratio of 30:70 (weight ratio), and thus, it is difficult to separate the mixture by distillation under normal pressure.

Thus, many investigations have been carried out about the method for purifying dimethyl carbonate from the mixture of the both components, and various proposals have been made. For example, there has been proposed the method of obtaining crystalline product enriched in dimethyl carbonate by cooling as disclosed in U.S. Pat. No. 3,803,201, the method of subjecting to separation of the mixture by distillation by breaking azeotrope with pressurization as disclosed in Japanese Patent Publication No. 3463/1984, and the method of subjecting to separation by distillation by adding a hydrocarbon such as hexane and heptane as disclosed in Japanese Unexamined Patent Publication No. 41820/1979. However, these methods cannot be said to be industrially satisfied. That is, the method of using extraction and distillation with water is not economical since dimethyl carbonate dissolves well in water and easily saponified so that causing many loss. An apparatus to be used in the method of distillation under pressure becomes extremely high cost and operations thereof are difficult. Also, the method of adding hydrocarbon is complicated in operations and disadvantageous in energy. Further, the method of precipitation by cooling is industrially not practical.

SUMMARY OF THE INVENTION

An object of the present invention is to provide a process for purifying dimethyl carbonate which can give high quality dimethyl carbonate by cancelling azeotropic phenomenon of dimethyl carbonate and methanol, and distilling and separating methanol easily.

The present inventors have intensively investigated, and consequently have found that dimethyl carbonate and methanol do not constitute azeotropic composition in the three-component system of dimethyl oxalate, dimethyl carbonate and methanol whereby accomplished the present invention.

That is, the present invention is a process for purifying dimethyl carbonate which comprises distilling a mixture of dimethyl carbonate and methanol in the presence of dimethyl oxalate to separate and remove methanol from the mixture.

DESCRIPTION OF THE PREFERRED EMBODIMENTS

In the following, the present invention is to be described in more detail.

An amount of dimethyl carbonate and methanol is not particularly limitative. An amount of dimethyl oxalate to be added is preferably 0.3 or more, particularly preferably 0.5 or more in terms of a mole fraction of dimethyl oxalate in the three components in order to enhance separation efficiency. In view of separation efficiency, there is no upper limit thereof, and it should be considered the range which can be industrially practiced, e.g. 0.8 to 0.9 in terms of a mole fraction of dimethyl oxalate in the three components.

In the three component system of dimethyl carbonate, dimethyl oxalate and methanol, dimethyl carbonate and methanol do not cause azeotropic phenomenon, so that methanol can be separated by distillation under normal pressure. Next, the mixture of dimethyl carbonate and dimethyl oxalate remained can be separated by the normal distillation to give dimethyl carbonate separated. Dimethyl oxalate remained can be used again by circulating the system.

Figure 2:
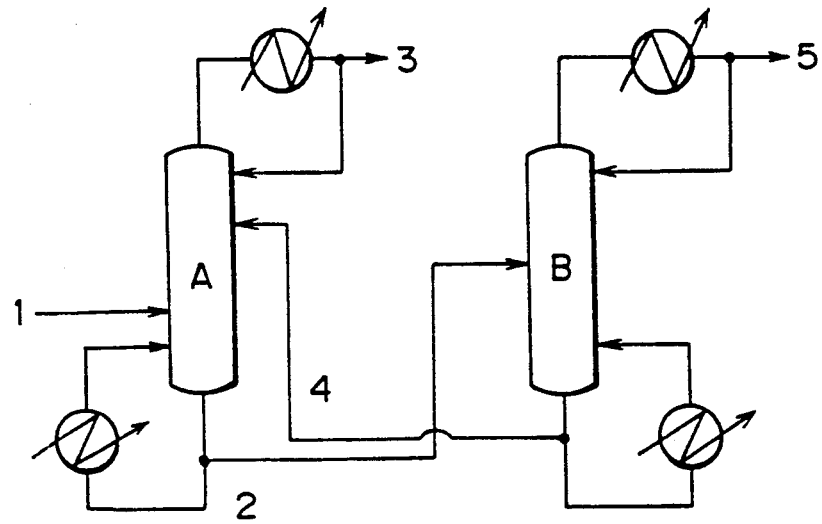
FIG. 2 shows a processing diagram of the continuous preparation process.

An industrial process of the present invention can be practiced by using a continuous apparatus as shown in FIG. 2. In FIG. 2, a crude reaction mixture 1 which is a mixture of dimethyl carbonate and methanol is continuously fed to a first column can A and also a solution of dimethyl oxalate is fed continuously. The mixture is refluxed by heating the bottom of the column to effect continuous distillation and methanol is taken out from the top of the first column distilled solution 3. A first column can solution 2 of the bottom is a mixture of dimethyl carbonate and dimethyl oxalate and it is fed to a second column can B and refluxed to effect continuous distillation whereby dimethyl carbonate is taken out from the top thereof as a second column distilled solution 5. A second tower can solution 4 at the bottom thereof is dimethyl oxalate as a distillation residue and it is returned to the first column can A to use again by circulation whereby continuous operation can be done.

When the process of the cresent invention is effected, if water exist in the distillation system, dimethyl oxalate is hydrolyzed so that water should previously be removed, if necessary. In the processes for preparing dimethyl carbonate as mentioned above, water is substantially not contained in the reaction product obtained by the method prepared from a cyclic carbonate or the method using a nitrite. Also, in the latter method, dimethyl oxalate is contained as a by-product in a little amount so that the reaction product prepared by the method can be applied to the purifying process of the present invention directly. By the reason as mentioned above, dimethyl carbonate can be prepared advantageously by the latter method as compared to the reaction product obtained by the other method.

Figure 1:
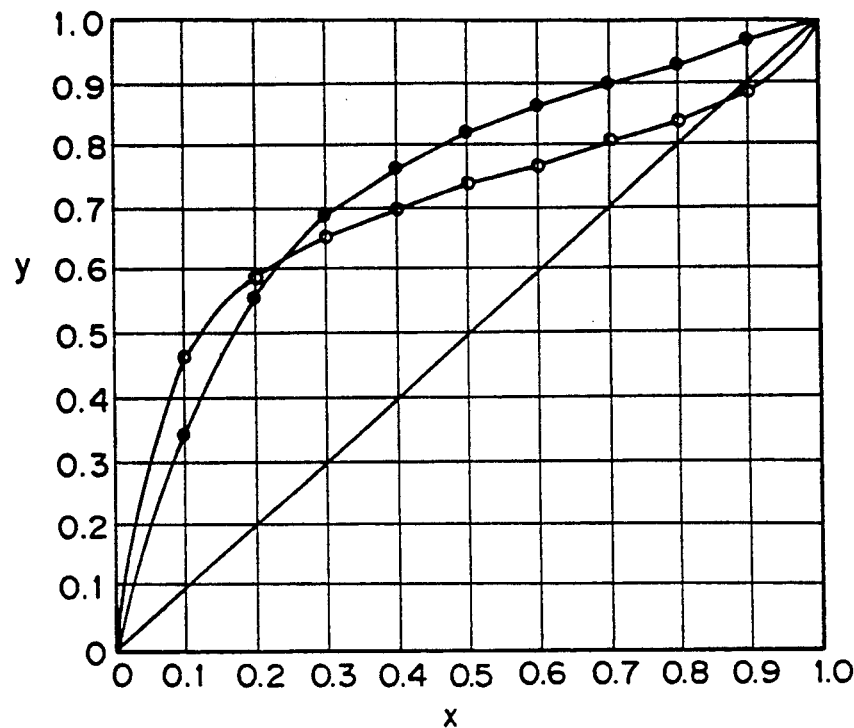
FIG. 1 is a graph showing the measured results of gas-liquid equilibrium of dimethyl carbonate and methanol.

In the three-component system comprising dimethyl oxalate, dimethyl carbonate and methanol according to the process of the present invention, dimethyl carbonate and methanol do not constitute azeotropic material. FIG. 1 is a graph of the measured results of gas-liquid equilibrium showing the matter, and it shows that by addition of dimethyl oxalate, separation by distillation of dimethyl carbonate and methanol becomes easy.

EXAMPLES

In the following, the process of the present invention will explained specifically by referring to Examples, but the present invention is not limited by these Examples.

EXAMPLE 1

To 6th step from the bottom of 50 steps oldershaw having an inner diameter of 32 mm was continuously fed a solution of 70% by weight of methanol and 30% by weight of dimethyl carbonate in an amount of 120 g per hour. At the same time, to 6th step from the top thereof, dimethyl oxalate dissolved by heating was continuously fed in an amount of 950 g per hour. Continuous operation was carried out by heating the bottom and a reflux ratio of about 5 and when the system became steady state (top temperature: 64.7° C. bottom temperature: 151.3° C.), a distilled solution from the top and a bottom solution were analyzed by gas chromatography. As the results, the distilled solution from the top contained 98.8% by weight of methanol and 1.2% by weight of dimethyl carbonate and the bottom solution contained 0.1% by weight of methanol, 3.5% by weight of dimethyl carbonate and 96.4% by weight of dimethyl oxalate. Also, a distilled amount at the too and an amount taken out from the bottom at the steady state were 83 g/hr and 986 g/hr, respectively.

EXAMPLE 2

The bottom solution taken out in Example 1 was continuously fed to 25th from the top of the same shape oldershow in an amount of 986 g per hour and continuous distillation was carried out with a reflux ratio of 4.7. When the system became steady state (top temperature: 86.2° C., bottom temperature: 166.4° C.), a distilled solution from the top and a bottom solution taken out were analyzed by gas chromatography. As the results, the distilled solution from the top contained 2.8% by weight of methanol and 97.2% by weight of dimethyl carbonate and the distilled amount was 35 g/hr. Also, the bottom solution contained substantially 100% by weight of dimethyl oxalate and the taken out amount was 949 g/hr.

EXAMPLE 3

The same procedure was carried out as in Example, 1 except for changing the composition of the feed solution to 21.3% by weight of methanol and 78.7% by weight of dimethyl carbonate and an amount of dimethyl oxalate to be fed was made 400 g per hour. As the results, a flow amount of the distilled solution at the top was 26 g/hr and the composition thereof was 97.7% by weight of methanol and 2.3% by weight of dimethyl carbonate. Also, a taken out amount of the bottom solution was 493 g/hr and the composition thereof was 0.04% by weight of methanol, 19.0% by weight of dimethyl carbonate and 81.0% by weight of dimethyl oxalate.

Comparative example 1 (the case that dimethyl oxalate is not added)

A solution of 70% by weight of methanol and 30% by weight of dimethyl carsonate was continuously fed without feed of dimethyl oxalate as in Example 1, and then the bottom was heated. The continuous operation was carried out at a reflux ratio of about 5, and when the system became the steady state, the top distilled solution and the bottom solution were analyzed by a gas chromatography. As a result, both top distilled solution and bottom solution had a composition of 70% by weight of methanol and 30% by weight of dimethyl carbonate.

According to the present invention methanol can be distilled and separated under normal pressure by breaking azeotrope of dimethyl carbonate and methanol, and dimethyl oxalate added can be circulated by recovering it and the process can be carried out continuously. Therefore, the process of the present invention is extremely excellent as an industrial process.

We claim:
1. A process for purifying dimethyl carbonate which comprises:
   (a) (1) continuously feeding a crude reaction mixture 1 which is a mixture mainly comprising dimethyl carbonate and methanol to a first column can A, and
   (2) simultaneously and continuously feeding a solution of dimethyl oxalate to the first column can A from the bottom of a second column can B wherein said dimethyl oxalate is added in an amount of 0.3 or more in terms of a mole fraction;
   (b) refluxing the mixture by heating the bottom of the first column to effect continuous distillation, removing methanol from the top of the first column as a first column distilled solution 3,
   (c) feeding a first column can solution 2 at the bottom thereof which is a mixture of dimethyl carbonate and dimethyl oxalate to the second column can B,
   (d) refluxing the mixture of dimethyl carbonate and dimethyl oxalate to effect continuous distillation, removing dimethyl carbonate from the top of the second column as a second column distilled solution 5, and
   (e) returning a second column can solution 4 at the bottom thereof which is dimethyl oxalate as a distillation residue to the first column can A.

2. The process according to claim 1, wherein dimethyl oxalate is added in an amount of 0.5 or more in terms of a mole fraction.

3. The process according to claim 1, wherein distillation is carried out under normal pressure.

4. The process according to claim 1, wherein said dimethyl carbonate is prepared by the method of using a nitrite.

* * * * *